(12) United States Patent
Picha (10) Patent No.: US 7,833,204 B2
(45) Date of Patent: Nov. 16, 2010

(54) INTRAMEDULLARY ACCESS OR INFUSION DEVICES

(75) Inventor: George J. Picha, Independence, OH (US)

(73) Assignee: Applied Medical Research, Brecksville, OH (US)

( * ) Notice: Subject to any disclaimer, the term of this patent is extended or adjusted under 35 U.S.C. 154(b) by 0 days.

(21) Appl. No.: 12/119,867

(22) Filed: May 13, 2008

(65) Prior Publication Data

US 2008/0287910 A1 Nov. 20, 2008

Related U.S. Application Data

(60) Provisional application No. 60/917,787, filed on May 14, 2007.

(51) Int. Cl.
*A61M 37/00* (2006.01)
(52) U.S. Cl. ............ 604/288.01; 606/92; 623/16.11; 623/17.12
(58) Field of Classification Search ............ 604/288.01, 604/288.02, 288.03, 288.04, 16, 40; 623/16.11, 623/17.12; 606/92
See application file for complete search history.

(56) References Cited

U.S. PATENT DOCUMENTS

| | | | |
|---|---|---|---|
| 3,136,316 A | 6/1964 | Beall | |
| 3,626,950 A | 12/1971 | Schulte | |
| RE27,310 E | 3/1972 | Hakim | |
| 4,579,555 A | 4/1986 | Russo | |
| 4,772,261 A | 9/1988 | Von Hoff et al. | |
| 4,850,953 A * | 7/1989 | Haber et al. | ................ 600/32 |
| 4,969,870 A | 11/1990 | Kramer et al. | |
| 5,122,114 A | 6/1992 | Miller et al. | |
| 5,163,924 A | 11/1992 | Beverly | |
| 5,207,709 A | 5/1993 | Picha | |
| 5,236,453 A | 8/1993 | Picha | |
| 5,312,364 A | 5/1994 | Jacobs | |
| 5,332,398 A | 7/1994 | Miller et al. | |

(Continued)

FOREIGN PATENT DOCUMENTS

DE 35 36 178 4/1987

OTHER PUBLICATIONS

"Ready, Aim, Fire! New IO device simplifies vascular access in sever cases," Jeff Lindsey, Jems, Feb. 2003, pp. 97-100.
"Long-term effects on tibial growth after intraosseous infusion: a prospective, radiographic analysis," I. Claudet et al., Pediatric Emergency Care, vol. 19, No. 6, Dec. 2003, pp. 397-401.
"Clinical review: vascular access for fluid infusion in children," Nikolaus A. Haas, Critical Care, vol. 8, No. 6, Dec. 2004, pp. 478-484.

(Continued)

*Primary Examiner*—Kevin C Sirmons
*Assistant Examiner*—Deanna K Hall
(74) *Attorney, Agent, or Firm*—Pearne & Gordon LLP (57) ABSTRACT

Intramedullary access or infusion devices that includes a tubular conduit having a distal end and a proximal end with a length sufficient to pass through the cortical region to the cancellous region of a bone; a flange circling the outside of the proximal end of the conduit; and a penetrable diaphragm positioned within the tubular conduit, are described. The devices may be placed in bone and later used, for example, as a site for administering a pharmacologically active agent.

13 Claims, 4 Drawing Sheets

U.S. PATENT DOCUMENTS

| | | | |
|---|---|---|---|
| 5,368,046 A | 11/1994 | Scarfone et al. | |
| 5,372,583 A | 12/1994 | Roberts et al. | |
| 5,591,188 A | 1/1997 | Waisman | |
| 5,817,052 A | 10/1998 | Johnson et al. | |
| 5,868,711 A | 2/1999 | Kramer et al. | |
| 5,868,747 A | 2/1999 | Ochoa et al. | |
| 5,960,797 A | 10/1999 | Kramer et al. | |
| 5,990,382 A | 11/1999 | Fox | |
| 6,018,094 A * | 1/2000 | Fox | 606/191 |
| 6,030,389 A | 2/2000 | Wagner et al. | |
| 6,071,310 A * | 6/2000 | Picha et al. | 623/17.11 |
| 6,106,495 A | 8/2000 | Scott | |
| 6,106,558 A | 8/2000 | Picha | |
| 6,228,088 B1 * | 5/2001 | Miller et al. | 606/80 |
| 6,346,122 B1 * | 2/2002 | Picha et al. | 623/17.11 |
| 6,387,098 B1 | 5/2002 | Cole et al. | |
| 6,458,117 B1 | 10/2002 | Pollins, Sr. | |
| 6,719,738 B2 | 4/2004 | Mehier | |
| 7,097,662 B2 | 8/2006 | Evans, III et al. | |
| 7,217,283 B2 | 5/2007 | Pedrozo et al. | |
| 7,608,062 B2 * | 10/2009 | Sweeney | 604/264 |
| 2002/0143317 A1 * | 10/2002 | Glossop | 604/529 |
| 2003/0225411 A1 | 12/2003 | Miller | |
| 2005/0131345 A1 | 6/2005 | Miller | |
| 2006/0015066 A1 | 1/2006 | Turieo et al. | |
| 2006/0052782 A1 | 3/2006 | Morgan et al. | |
| 2006/0149362 A1 | 7/2006 | Pedrozo et al. | |
| 2006/0247773 A1 | 11/2006 | Stamp | |

OTHER PUBLICATIONS

"Sternal intraosseous infusions, Emergency vascular access in adults," Mary Jo Koschel, AJN, vol. 105, No. 1, Jan. 2005, pp. 66-68.

"Intraosseous vascular access in the treatment of chemical warfare casualties assessed by advanced simulation: proposed alteration of treatment protocol," Amir Vardi et al., Anesth Analg, 98, 2004, pp. 1753-1758.

"Tibial fracture as a complication of intraosseous infusion during pediatric resuscitation," Douglas M.G. Bowley et al., J. Trauma, 2003, 55, pp. 786-787.

"Hypertonic saline: Intraosseous infusion causes myonecrosis in a dehydrated model of uncontrolled hemorrhagic shock," Hasan B. Alam et al., The Journal of Trauma Injury, Infection, and Critical Care, Jan. 2002, vol. 52, No. 1, pp. 18-25.

"Adult IO arrives, The solution to difficult vascular access," A.J. Heightman, Elsevier/Jems, 2005.

"Intraosseous infusion devices: A comparison for potential use in special operations," Mark D. Calkins et al., The Journal of Trauma: Injury, Infection, and Critical Care, vol. 48, No. 6, pp. 1068-1074.

* cited by examiner

INTRAMEDULLARY ACCESS OR INFUSION DEVICES

CROSS-REFERENCE TO RELATED APPLICATION

The present application claims the benefit of U.S. Provisional Application Ser. No. 60/917,787 filed May 14, 2007, which is incorporated by reference herein in its entirety.

BACKGROUND OF THE INVENTION

Drugs and other liquids are customarily delivered to patients via their vascular systems, using a needle or catheter inserted into a peripheral blood vessel. Such techniques are generally satisfactory when the patient's blood pressure is at normal levels, and blood vessels can be readily located. However, in cases where the patient is in circulatory shock as a result of, for example, heart failure, drug overdose, or severe hemorrhaging, the peripheral blood vessels are frequently collapsed and access to the blood vessels is difficult. Furthermore, blood vessels may be difficult to locate under stress or other adverse conditions. Substantial delays in administering the drugs and liquids can therefore result and, in many instances, vascular access cannot be obtained at all. Severe injury to the patient or even death can result.

A suitable alternative to vascular infusion that is particularly useful when peripheral blood vessels are collapsed is intraosseous infusion. This technique first saw significant use during World War II, when sternal puncture kits for bone marrow infusions were included in emergency medical supplies, but has only recently been given significant attention in the medical literature. In intraosseous infusion, a resuscitative fluid or drug solution is injected directly into the bone marrow of the patient's bone, from where it is transported throughout the patient's body. Intraosseous infusion requires penetration of the patient's skin and outer bone by a needle or the like to gain access to the intraosseous space.

The intraosseous space within bone is often referred to as a non-collapsible vein. Bone consists of an outer layer of cortical bone and an inner medullary marrow cavity containing cancellous (i.e. spongy) bone tissue. The inner cavity is also referred to as the intraosseous space. The intraosseous space contains thousands of tiny non-collapsible blood vessels, and will transport substances quickly, generally within seconds, to the central veins in the body. Infants and children have only red marrow in the intraosseous space, which is gradually replaced with yellow marrow in the bones of adults. Blood flow through the intraosseous space is relatively constant, even in most cases of shock, and blood pressure is typically about 35/25 mmHg, which is about a third of systemic arterial blood pressure.

Among the earliest devices for intraosseous (IO) infusion were manually inserted IO devices. These devices included modified steel needles with removable trocars to prevent plugging with bone fragments and special handles to allow the operator to push into the bone while rotating. These devices were used primarily in pediatrics because children's bones are softer than adults and children's blood vessels are often particularly difficult to locate. More recently, IO infusion devices have been developed for IO infusion for adults. These include the First Access for Shock and Trauma (FAST), described in U.S. Pat. No. 5,817,052, and the Bone Injection Gun (BIG), described in U.S. Pat. No. 5,591,188. These are both impact-driven devices in which a powerful spring drives a needle into the bone to a certain depth. More recently, a battery-powered IO access device using a specially designed drill-tipped need has been developed, in which a battery-powered motor drives the needle into the bone, as described in U.S. patent application Ser. No. 10/449,476, entitled "Apparatus and Method to Access Bone Marrow." However, these devices all require the bone to be penetrated at the time IO infusion is needed, and can be stymied by various problems such as bent needles, operator inexperience, or even failed power supplies.

SUMMARY OF THE INVENTION

In one aspect, the present invention provides an intramedullary access device that includes a tubular conduit having a distal end and a proximal end with a length sufficient to pass through the cortical region to the cancellous region of a bone. The intramedullary access device also includes a flange circling the outside of the proximal end of the conduit and a penetrable diaphragm positioned within the tubular conduit.

Embodiments of the intramedullary access device include those in which the outside of the tubular conduit includes surface texturing. In another embodiment, the outside of the tubular conduit includes threading. In embodiments with threading, the threading can also include micropillars. In a further embodiment, the length of the tubular conduit is from about 1 mm to about 10 mm. In yet another embodiment, the penetrable diaphragm includes an elastomer. In yet another embodiment, the device further includes a sensor. In other embodiments, the device can include a magnetic material.

In another aspect, the present invention provides an intramedullary infusion device that includes a tubular conduit having a distal end and a proximal end with a length sufficient to pass through the cortical region and extend into the cancellous region of a bone; wherein the tubular conduit is closed at the distal end. The intramedullary infusion device also includes a flange circling the outside of the proximal end of the conduit; a penetrable diaphragm positioned within the tubular conduit; one or more outlet openings positioned along the tubular conduit in the region that will extend into cancellous bone; and a compressible member positioned over the outlet openings at the distal end of the tubular conduit.

Embodiments of the intramedullary infusion device can include outlet openings that are positioned on outlet structures that extend beyond the surface of the tubular conduit. In other embodiments, the compressible member includes an elastomer. In another embodiment, the compressible member includes a spring-loaded diaphragm. In yet another embodiment, the outside of the tubular conduit includes surface texturing. In a further embodiment, the outside of the tubular conduit includes threading. In embodiments including threading, the threading can include micropillars. In yet a further embodiment, the device can include a sensor.

Another aspect of the present invention provides a method of intramedullary drug delivery that includes detecting an intramedullary access device in the bone of a patient; inserting a needle through the penetrable diaphragm of the intramedullary access device; and administering a drug through the intramedullary access device into the cancellous bone of the patient.

Yet another aspect of the present invention provides a method of intramedullary drug delivery that includes detecting an intramedullary infusion device in the bone of a patient; applying pressure to the compressible member of the intramedullary infusion device to expose an outlet opening; and administering a drug through the intramedullary infusion device into the cancellous bone of the patient.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

It is understood that all spatial references, such as "horizontal," "vertical," "top," "upper," "lower," "bottom," "left," and "right," are for illustrative purposes only and can be varied within the scope of the disclosure.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4 is a cross-sectional view of an intramedullary infusion device including a compressible member, in which

The following detailed description is to be read with reference to the figures, in which like elements in different figures have like reference numerals. The figures, which are not necessarily to scale, depict selected embodiments and are not intended to limit the scope of the invention. Skilled artisans will recognize the embodiments provided herein have many useful alternatives that fall within the scope of the invention.

DETAILED DESCRIPTION OF EMBODIMENTS OF THE INVENTION

The following discussion is presented to enable a person skilled in the art to make and use the invention. Various modifications will be readily apparent to those skilled in the art, and the general principles disclosed herein may be applied to other embodiments and applications without departing from the scope of the present invention as defined by the appended claims. Thus, the present invention is not intended to be limited to the embodiments shown, but is to be accorded the widest scope consistent with the principles and features disclosed herein.

Figure 1:
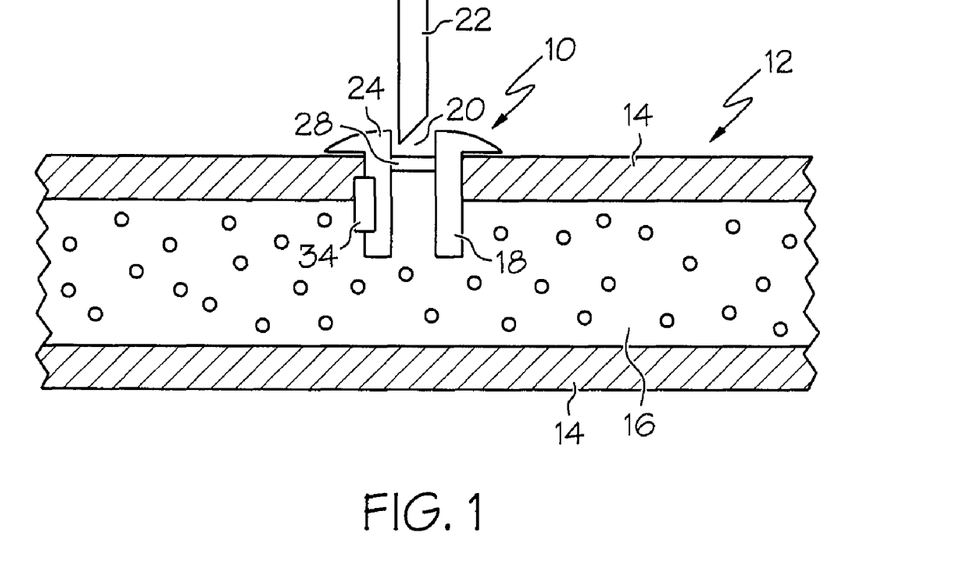
FIG. 1 is a cross-sectional view of an embodiment of the intramedullary access device positioned to penetrate into the intramedullary region of a bone.
Figure 2:
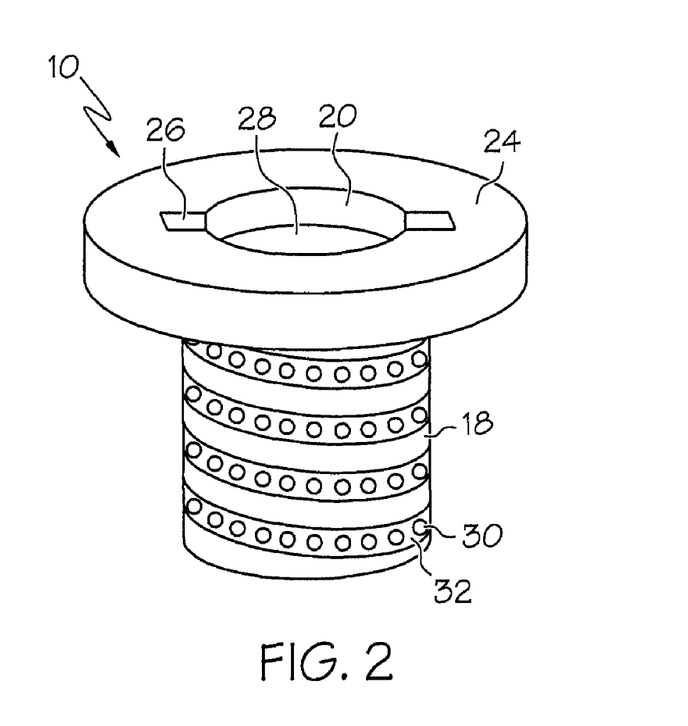
FIG. 2 is a perspective view of an intramedullary access device with threading formed of micropillar columns.

The present invention relates to implantable devices that facilitate intramedullary access for intraosseous infusion. Referring to FIGS. 1 and 2, an exemplary embodiment of an intramedullary access device 10 of the present invention is shown. FIG. 1 shows an intramedullary access device 10 that has been placed in a bone 12. The bone 12 includes a cortical region 14 of relatively dense bone and an underlying region of cancellous bone 16. Cancellous bone 16, also known as trabecular or spongy bone, is an osseous bone tissue with low strength and density, including numerous pockets that provide it with a high surface area. The intramedullary access device 10 includes a tubular conduit 18 with a distal end and a proximal end, and a length sufficient to pass through the cortical region 14 of bone tissue and into the cancellous bone 16.

The tubular conduit 18 may be provided in a variety of different lengths to accommodate variations in the thickness of the cortical bone. For example, the tubular conduit 18 may have a length from about 1 millimeter (mm) to about 10 mm, or alternately a length from about 3 mm to about 5 mm. The tubular conduit 18 includes an outside surface extending from its proximal end to its distal end along a longitudinal axis. The tubular conduit 18 also includes a tunnel 20 that runs through the center of the tubular conduit 18 along the longitudinal axis. The tunnel 20 should be wide enough to accommodate a needle 22 or similar device used to administer a pharmaceutically active agent to the cancellous bone 16. For example, the tunnel 20 may have a width of about 3 mm to about 10 mm. The tubular conduit 18 surrounding the tunnel 20 may have an overall diameter of up to 1 cm, with some embodiments having diameters from about 5 mm to about 10 mm.

The proximal end of the tubular conduit 18 includes a flange 24 that circles the proximal end of the conduit 18. The flange 24 may provide several advantageous functions, including sealing the gap between the bone 12 and the device 10 to prevent leakage to or from the intramedullary space, infection of the bone or surrounding tissue, over-insertion of the device 10 into the bone 12, and also provides a protrusion on the surface of the bone 12 that can aid in locating the device 10 by palpitation. The flange 24 also provides a surface that can be readily modified to facilitate insertion of the intramedullary access device 10 by tools such as device drivers. For example, the flange 24 may be provided with a slot 26 as shown in FIG. 2. Alternately, one or more slots 26 may be provided elsewhere on the flange 24, such as along the circumference of the flange 24.

The intramedullary access device 10 may be formed using any suitable biocompatible polymer, metal, or ceramic known to those skilled in the art. For example, suitable biocompatible material including metals such as cobalt-chromium alloys, titanium alloys, nickel titanium alloys, and/or stainless steel alloys. In some embodiments, at least a portion of the intramedullary access device 10 can be formed of magnetic material to facilitate its detection. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

The intramedullary access device 10 generally includes a penetrable diaphragm 28 positioned within the tunnel 20 of the tubular conduit 18. The diaphragm 28 seals the tunnel of the intramedullary access device 10 to prevent leakage to and from the intramedullary region, and/or to prevent infection. The diaphragm may be retained within the tubular conduit 18 by, for example, using adhesives or threading that fits within the tunnel 20. The diaphragm 28 should be penetrable to allow a needle or similar device to penetrate through the diaphragm so that the intramedullary region may be accessed to deliver pharmacologically active agent or obtain samples (e.g., blood samples). The penetrable diaphragm 28 may be formed from, for example, an elastomer selected from the group consisting of polyurethane, styrene butadiene styrene, or silicone. Alternately, a guide port and a flapper valve together with a flapper strike plate may be used in place of a penetrable diaphragm 28 within the tunnel 20.

The outside surface of the tubular conduit 18 may be smooth, or it may include texturing 30 and/or threading 32. Including texturing and/or threading can provide better integration, reduce shear stress, and/or improve fixation to the bone. In some embodiments, threading and texturing may be combined, such that either the threads are formed from texturing or they include additional texturing on the surface of the threads.

Generally, the screw threads included are of a conventional design. Accordingly, they consist of a generally helical thread 32 that winds along the length of the outside surface of the tubular conduit 18. A single continuous thread can be used, or plural parallel threads or interrupted thread segments may be employed as is known in the art. While threading may simply be provided along the length of the tubular conduit 18, threading that allows the intramedullary access device 10 to function as a self-tapping screw may also be used. Self-tapping threading may narrow to a point and including notching at the distal end of the tubular conduit 18, and provide the advantage of making their own threads as the threaded tubular conduit 18 is screwed into a bore drilled into bone 12. Various types of screw threading, and threading including surface texturing, is described in U.S. Pat. No. 5,868,747, which is incorporated herein by reference.

The intramedullary access device 10 can also include texturing 30 on the outer surface of the tubular conduit 18 to enhance the fixation of the device 10. For example, the surfaces may be roughened such as by chemical etching, bead-blasting, sanding, grinding, serrating, and/or diamond-cutting. The surface texturing can be of small magnitude so that it does not abrade the bone surface, with the texturing extending outward from the surface so that the area of contact with bone is reduced, at least upon initial insertion. After insertion, when the bone has had an opportunity to relax or decompress and conform to the textured surface, a larger surface area contacts bone, making removal more difficult. Surface texturing with specific geometries can also be provided. Such surface texturing can be asymmetric or anisotropic, with angled features that facilitate installation or discourage loosening. This type of surface texturing may be provided by a variety of methods, such as directed sputtering by ion beam bombardment, ion beam bombardment through a pattern defining mask, sputter-etching, or machining.

Alternately, or in addition, larger surface texturing may be included. Larger texturing may be used to provide surface features such as threading. For example, as shown in FIG. 2, the intramedullary access device can include a helical thread projecting from the outside surface of the tubular conduit 18 comprising a plurality of micropillars projecting therefrom. Alternatively, a plurality of micropillars may project from the exterior surface of the shell in a regular, non-helical array. The pillars may be cylindrical, square, rectangular, or crescent-shaped. Use of micropillars to provide threading is described in U.S. Pat. No. 6,071,310, which is incorporated herein by reference.

All or a portion of the outer surface of the tubular conduit 18 may also be provided with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes for initial fixation; ridges or keels to prevent migration in the lateral and anterior direction, for example; serrations or diamond cut surfaces; fins; posts; and/or other surface textures.

Figure 3:
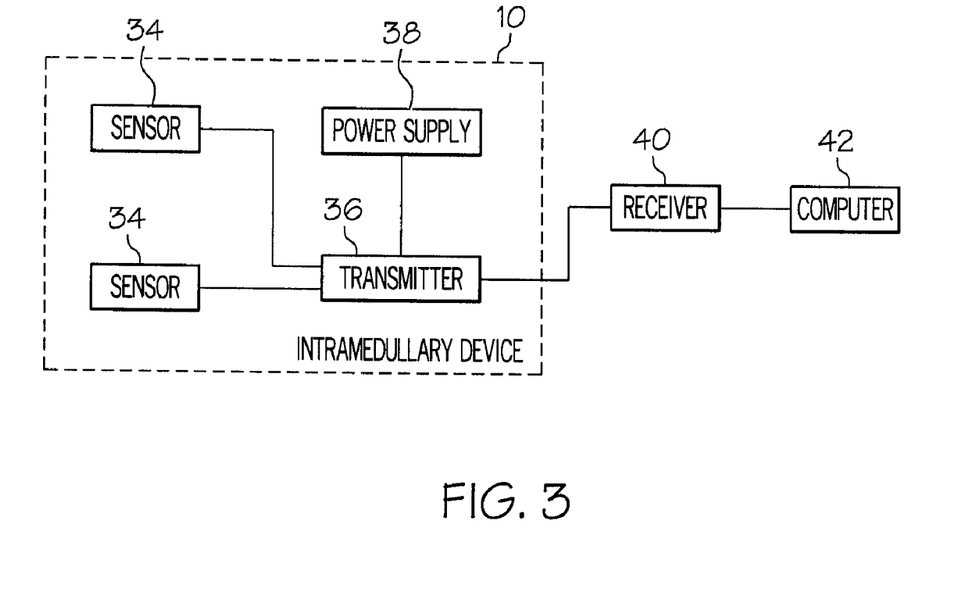
FIG. 3 is a diagram of a sensor system that may be used with the intramedullary access device.

The intramedullary access device 10 can be fitted with various diagnostic sensors 34 in order to detect one or more physical parameters. The detected parameters may include, for example, pressure, linear displacement, angular displacement, temperature, pH, or glucose metabolic chemistries. A system for analyzing physical parameters using sensors associated with an intramedullary access device 10 is shown in FIG. 3. The intramedullary access device may include one or more sensors 34 coupled to a biotelemetry transmitter 36. Multiple sensors 34 may be used to measure multiple physical parameters simultaneously. The sensors 34 can include microscopic sensing element or elements fabricated using semiconductor or MEMS (microelectromechanical systems) fabrication technology.

The intramedullary access device 10 may further include a transmitter 36 which may be wired or wirelessly coupled to the sensors 34. It is understood that additional components such as power components, memory components, a CPU, or additional transmitters may be incorporated in the device 10 as needed. Referring again to FIG. 3, the system can also include a power supply 38 associated with the transmitter 36. The power supply 38 and the transmitter 36 are shown as being incorporated into the intramedullary access device 10, but they can also be provided external to the device 10. Several methods are available to power the sensor 34 remotely. For example, the sensor 34 can be powered remotely using magnetic or RF induction. The analog data from the sensor 34 will be converted to frequency and will be transmitted using a low-power RF transmitter. Alternately, a self-power generating system including substituting stacks of piezoelectric material can be included. See for example U.S. Pat. No. 7,097,662, which is incorporated herein by reference.

The system can further include a receiver 40 in communication with the transmitter 36. The transmitter 36 and the receiver 40 may communicate data about the physical parameters detected by the one or more sensors 34 through telemetry or percutaneous wires (e.g., RF signals). The receiver 40 may be connected to a computer 42 for processing the received data about the physical parameters detected by the sensors 34. Further information regarding sensors suitable for inclusion in implanted orthopedic devices can be found in U.S. patent application Ser. Nos. 11/118,170 and 11/147,750, which are incorporated herein by reference.

Figure 4A:
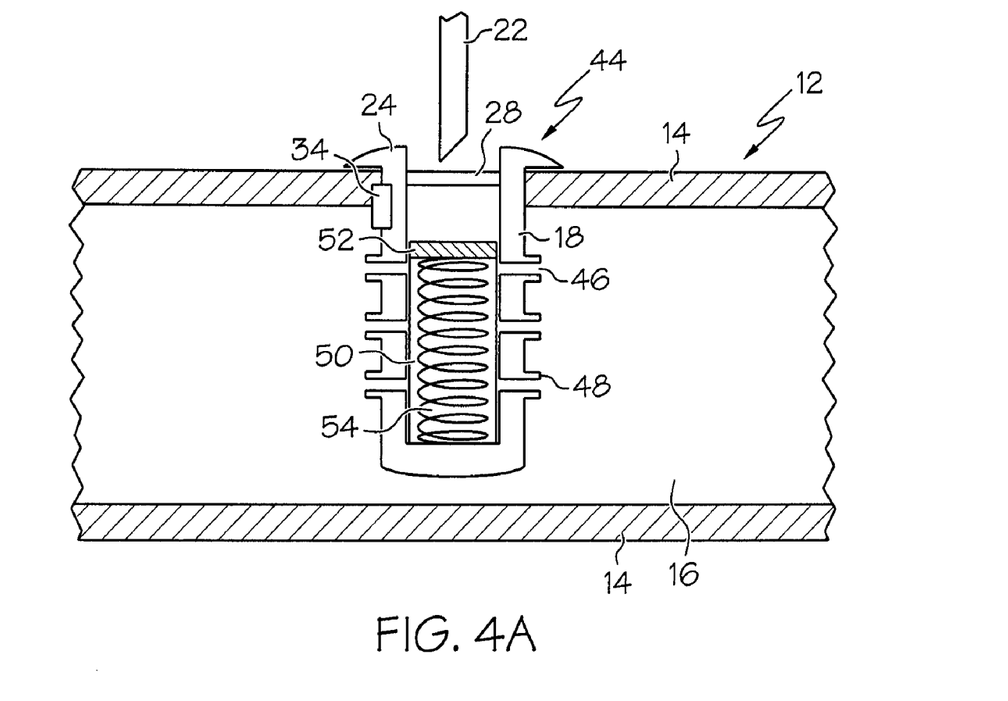
FIG. 4A shows the device before the compressible member has been compressed and FIG. 4B shows the device after the compressible member has been compressed and drug is being delivered.
Figure 4B:
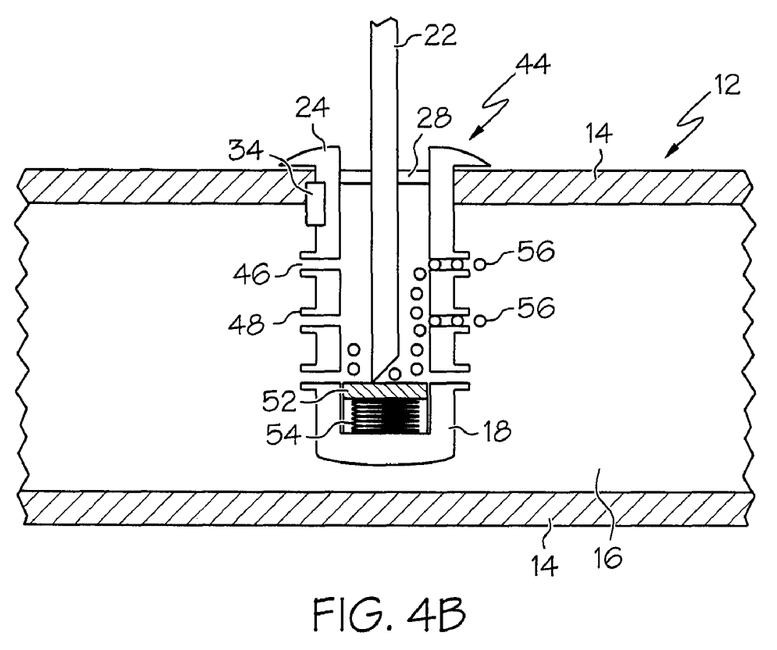
Figure 5:
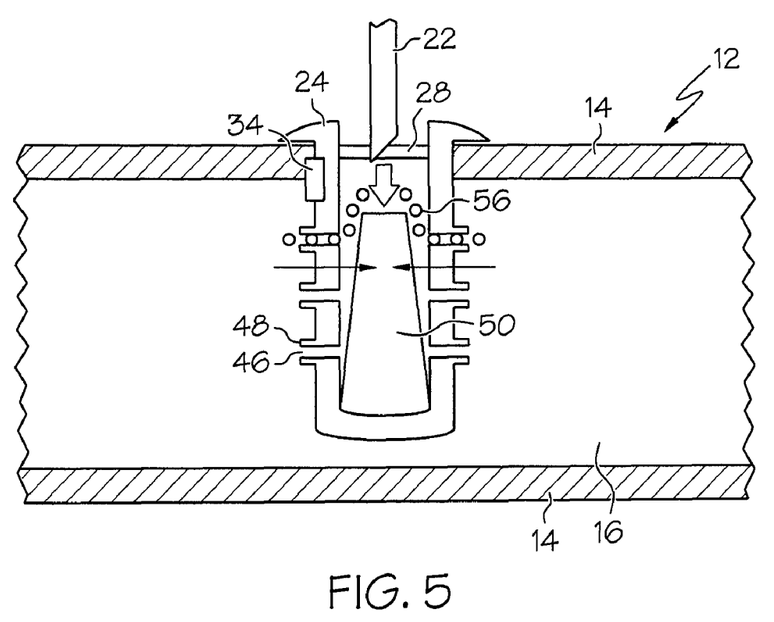
FIG. 5 is a cross-sectional view of an embodiment of the intramedullary infusion device including a compressible member in which the delivered drug has compressed the compressible member to allow drug elution.
Figure 6A:
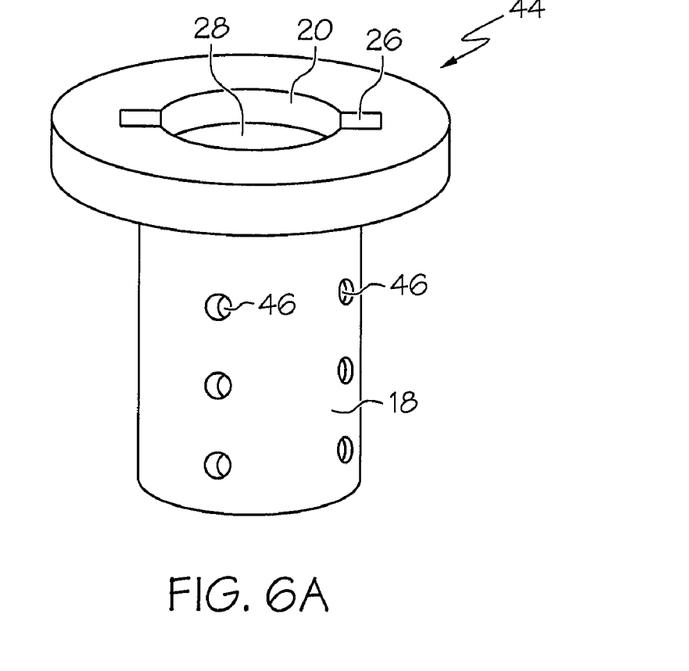
FIGS. 6A and 6B are perspective view of an intramedullary infusion device, without outlet structures (6A) and with outlet structures (6B).
Figure 6B:
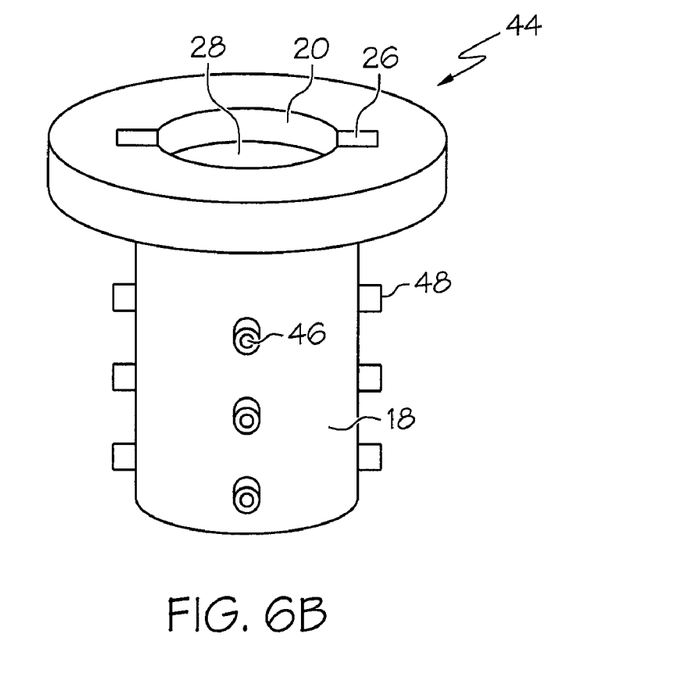

An additional embodiment of the intramedullary access device 10, referred to herein as the intramedullary infusion device 44, is shown in FIGS. 4-6. The intramedullary infusion device 44 includes a tubular conduit 18 with a distal end and a proximal end, and a flange 24 circling the outside of the proximal end of the conduit, as well as a penetrable diaphragm 28 positioned within the tubular conduit 18. In this embodiment, the tubular conduit is closed at the distal end. Furthermore, the tubular conduit 18 has a length sufficient to extend through the cortical region 14 of the bone 12 and extend into the cancellous 16 region. Since pharmacologically active agent may exit from the tubular conduit 18 along its sides rather than its distal end, the intramedullary infusion device 44 may have a length longer than that typically used for the intramedullary access device 10 described earlier herein. As with the intramedullary access device 10 described earlier, the intramedullary infusion device 44 can include one or more sensors 34.

One or more outlet openings 46 may be provided along the sides of the tubular conduit 18. The outlet openings 46 are in communication with the interior of the tubular conduit 18, and can accommodate the flow of fluid from the intramedullary access device 10 to the cancellous bone 16. The outlet openings 46 can have various sizes depending on the desired flow rate. For example, the outlet openings 46 can have a diameter from about 3 µm to 10 µm. Typically, a plurality of outlet openings 46 are provided to minimize resistance to the effusion of liquid from the intramedullary effusion device 44 and to help diffuse the release of such liquid. Because the outlet openings 46 are used for delivering fluid to the cancellous bone 16, the outlet openings 46 are not provided near the proximal end of the tubular conduit 18, but rather are positioned towards the distal end where they can be expected to contact the cancellous bone 16 upon insertion.

The outlet openings 46 may simply be channels that run through the sides of the tubular conduit 18, as shown in FIG. 6A. However, the outlet openings 46 can also be positioned so that they also run through an outlet structure 48 provided on the surface of the tubular conduit, as shown in FIG. 6B. The outlet structures 48 may have a variety of shapes, such as pillars (cylindrical, square, rectangular, etc.) or fins. The outlet structures 48 typically have a length from about 3 µm to about 15 µm. The outlet openings 46 extend through both the tubular conduit 18 and the outlet structures 48 and can facilitate fluid flow by extending beyond fibrous capsule formation that may occur around the intramedullary infusion device 44 after it has been placed in the bone that might otherwise block fluid flow.

The intramedullary infusion device 44 also includes a collapsible member 50 positioned over the outlet openings 46 when in its non-collapsed state. The collapsible member 50 functions to prevent flow into our out of the intramedullary infusion device 44 unless it is subject to pressure which moves it past the outlet openings 46. This is illustrated in FIGS. 4a, 4b, and 5. FIGS. 4a and 4b show an embodiment of the intramedullary infusion device 44 in which the collapsible member 50 is moveable diaphragm 52 that fits within the tubular conduit 18 and is supported by a spring 54. Alternately, the diaphragm 52 and the spring 54 may be replaced by other collapsible members 50 such as a compressible elastomer. In FIG. 4a, the intramedullary infusion device 44 is shown in its normal configuration, in which liquid cannot flow into or from the device because the outlet openings 46 are blocked by the collapsible member 50. However, as shown in FIG. 4b, when pressure is applied (e.g, by the needle 22) to compress the compressible member 50, the compressible member 50 moves towards the distal end of the tubular conduit, exposing one or more of the outlet openings 46. When this has occurred, liquid (e.g., liquid carrying a pharmacologically active agent 56) can flow from the intramedullary infusion device 44 to the surrounding cancellous region 16 of the bone 12. Alternately, upon compressing the compressible member 50, fluid may be drawn into the intramedullary infusion device 44 for collection.

FIG. 5 shows another embodiment of the intramedullary infusion device 44. The collapsible member 50 in this embodiment is capable of contracting inwards as well as compressing downwards in response to the application of pressure. Accordingly, as shown in FIG. 5, the application of pressure, as indicated by the large arrow, results in the collapsible member 50 contracting inwards, as indicated by the thin arrows, allowing liquid (e.g., liquid carrying a pharmacologically active agent 56) to flow past the collapsible member 50 and outwards into the surrounding cancellous region 16 of the bone.

The intramedullary access device 10 (including alternate embodiments, such as the intramedullary infusion device 44) can be inserted into the bone by various methods known to those skilled in the art. For example, a drill may first be used to bore a proper sized hole for fitting the device 10 into the bone 12. An incision is made in the skin of the patient, preferably after cleaning and administration of an anesthetic, and a hole is then drilled into the bone 12. The incision may be made at a position slightly offset from the location where the hole will be drilled in order to prevent the formation of scar tissue and/or inhibit subsequent infection at the infusion site where the device 10 is placed. The drill should have a drill bit with a spiral cutting edge suitable to cut and remove cortical and cancellous bone. The bore may be smooth or may be threaded, depending on the nature of the device 10 being used. The drilling may be done at low speed with good irrigation to minimize trauma to the bone. The intramedullary access device 10 may be placed in any location suitable for intraosseous infusion, such as the middle or the end portions of a bone. Specific sites suitable for intraosseous infusion include the proximal tibia and/or the sternum.

The device 10 can then be inserted by tapping it into place. The device 10 is typically inserted with the diaphragm 28 positioned within the device 10. However, the diaphragm 28 can also be placed in the device 10 subsequent to insertion. Note that embodiments including texturing 30 on the outer surface of the tubular conduit 18 can be readily inserted by tapping, and that the texturing 30 will help retain the inserted device in place. Biocompatible adhesives can also be used to help retain the intramedullary access device 10. Alternately, instead of inserting the device by tapping, it may be inserted by screwing it in if the device includes threading. The device 10 may be screwed in by engaging slots 26 within the flange 24 and then rotating a tool to screw the device 10 into the bone 20. The tool or device driver may be in the shape of a standard screw driver or standard orthopedic instrument handle with keys to accommodate the flange much like a socket wrench engages a nut.

Once insertion of the device 10 is complete, the skin can be sutured closed for subsequent percutaneous access by a needle 22. Preferably, the skin is allowed to heal prior to use of the device; however, the device 10 may be used immediately if necessary. In order to encourage healing of the skin, it may be desirable to position a thin sheet of biocompatible microporous polymeric material covering the region where the skin will be replaced after insertion of the device. Use of such polymeric material can help anchor the skin and avoid formation of deadspace that can lead to infection or other problems.

Once inserted, the intramedullary access device 10 remains in place until needed. However, should the device 10 become plugged, it can be removed and the area cleaned. For example, cutters (e.g., flexshaft driven) can be introduced to open the blockage and restore access to the blood vessels within the cancellous bone tissue, after which the device 10 can be re-inserted. Furthermore, should the penetrable diaphragm 28 become damaged, it can be replaced without removing the access device 10 and damaging the surrounding bone tissue. Replacement of the penetrable diaphragm 28 may, for example, be necessary if the diaphragm 28 has been damaged as a result of repeated use of the device 10.

As already described, the intramedullary access device 10 must be placed within the bone 12 before use. However, unlike conventional intraosseous infusion, where the bone often must be penetrated in an emergency situation outside of a clinical environment, the intramedullary access device 10 may be implanted at any convenient time by skilled medical personnel. Other advantages to the use of an intramedullary access device 10 include increased speed of use and decreased pain to the subject during use.

To use the intramedullary access device 10, it is first located by palpitation, markings, or knowledge regarding its typical placement. In the case of intramedullary access devices 10 that include a magnetic material, it may be detecting by locating the magnetic field or response to a magnetic field engendered by the device 10. Once located, a needle 22 is then properly oriented above the intramedullary access device 10 and then driven through the skin and soft tissue through the penetrable diaphragm 28 within the intramedullary access device 10, and into the cancellous bone 16. Preferably, the skin is prepared (e.g., cleaned) before the infusion needle 22 is inserted into the access device 10. Once the needle 22 has reached the cancellous bone 16, liquid may be delivered from the needle 22. The liquid is preferably delivered at a rate of about 100 mL/minute, though depending on the nature of the intraosseous space, lower delivery rates such as about 50 mL/minute may be used.

A variety of fluids and liquids carrying pharmacologically active agents 56 can be administered. For example, fluids such as hypertonic saline, blood, and lactated Ringer's solution may be administered. Pharmacologically active agents that may be administered include, for example, aminophylline, amiodarone, atropine, domapine, epinephrine, etomidate, fentanyl, levophed, lidocaine, promethezine, recuronium, succinylchonline, thiamine, vasopressin, chemotherapeutic agents, or any other drug that is typically administered intravenously. When fluid is delivered to a conscious patient, it may be preferable to co-administer a local anesthetic such as lidocaine to minimize visceral pain from pressure within the bone.

Note that in addition to delivering of drugs and fluids, the intramedullary access device 10 can also be used to provide a convenient access point for sampling blood chemistries, partial pressure of arterial carbon dioxide, pH, and hemogloblin counts, for example. In addition to providing a convenient access point, embodiments of the intramedullary access device 10 can also include sensors 34 to monitor various parameters of medical interest.

Once placed, the intramedullary access device 10 may be used as often as needed to provide access for intraosseous infusion. The intramedullary access device 10 may be left in place in the bone for as long as there is a significant chance that it will be needed. For example, for soldiers, the intramedullary access device 10 could be implanted before the soldiers enter combat and then removed at the end of their service. The intramedullary access device 10 is particularly valuable for individuals who are placed in high risk situations. Soldiers would also particularly benefit from ready intraosseous access, because acute hemorrhage is a major cause of battlefield death, and treatment must often be carried out hastily under high stress conditions upon soldiers in a hypotensive state with collapsed peripheral veins.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. An intramedullary infusion device, comprising:
   a tubular conduit having a distal end and a proximal end with a length sufficient to pass through the cortical region and extend into the cancellous region of a bone; wherein the tubular conduit is closed at the distal end;
   a flange circling the outside of the proximal end of the conduit;
   a penetrable diaphragm positioned within the tubular conduit;
   a plurality of outlet structures positioned along the outer side surfaces of the tubular conduit, wherein an outlet structure creates an outlet opening so as to allow fluid flow between the tubular conduit and the cancellous region of the bone; and
   a compressible member positioned over the outlet openings at the distal end of the tubular conduit, wherein the compressible member comprises an elastomer.

2. The intramedullary infusion device of claim 1, wherein the outlet openings are positioned on outlet structures that extend beyond the surface of the tubular conduit.

3. The intramedullary infusion device of claim 1, wherein the outside of the tubular conduit includes surface texturing.

4. The intramedullary infusion device of claim 1, wherein the outside of the tubular conduit includes threading.

5. The intramedullary infusion device of claim 4, wherein the threading comprises micropillars.

6. The intramedullary infusion device of claim 1, wherein the device further comprises a sensor.

7. An intramedullary infusion device, comprising:
   a tubular conduit having a distal end and a proximal end with a length sufficient to pass through the cortical region and extend into the cancellous region of a bone; wherein the tubular conduit is closed at the distal end;
   a flange circling the outside of the proximal end of the conduit;
   a penetrable diaphragm positioned within the tubular conduit;
   a plurality of outlet structures positioned along the outer side surfaces of the tubular conduit, wherein an outlet structure creates an outlet opening so as to allow fluid flow between the tubular conduit and the cancellous region of the bone; and
   a compressible member positioned over the outlet openings at the distal end of the tubular conduit, wherein the compressible member comprises a spring-loaded diaphragm.

8. The intramedullary infusion device of claim 7, wherein the outside of the tubular conduit includes surface texturing.

9. The intramedullary infusion device of claim 7, wherein the outside of the tubular conduit includes threading.

10. The intramedullary infusion device of claim 9, wherein the threading comprises micropillars.

11. The intramedullary infusion device of claim 7, wherein the device further comprises a sensor.

12. The intramedullary infusion device of claim 7, wherein the outlet openings are positioned on outlet structures that extend beyond the surface of the tubular conduit.

13. The intramedullary infusion device of claim 7, wherein the compressible member comprises an elastomer.

* * * * *